United States Patent [19]

Sugai et al.

[11] Patent Number: 6,063,366
[45] Date of Patent: May 16, 2000

[54] COSMETIC COMPOSITION

[75] Inventors: Ichiro Sugai; Akiko Suzuki; Tomohiko Sano; Kazuhiro Kaizu; Toshio Uesaka, all of Tokyo, Japan; Akira Fuji, Cincinnati, Ohio

[73] Assignee: Kao Corporation, Tokyo, Japan

[21] Appl. No.: 08/989,340

[22] Filed: Dec. 11, 1997

[30] Foreign Application Priority Data

Dec. 12, 1996 [JP] Japan ................................. 8-332019
Nov. 7, 1997 [JP] Japan ................................. 9-305718

[51] Int. Cl.⁷ ..................................................... C08G 63/00
[52] U.S. Cl. ........................ 424/69; 424/78.02; 424/195; 424/343; 424/359; 424/489
[58] Field of Search ................................ 424/195, 343, 424/359, 489, 69, 78.02

[56] References Cited

U.S. PATENT DOCUMENTS 3,691,281  9/1972  Battista ................................. 424/195

*Primary Examiner*—Terressa Mosley
*Attorney, Agent, or Firm*—Oblon, Spivak, McClelland, Maier & Neustadt, P.C.

[57] ABSTRACT

Disclosed herein is a cosmetic composition comprising disintegrating granules composed of water-insoluble primary particles and a binder, wherein the disintegrating granules in the cosmetic composition have a compression strength of 0.002–0.1 kgf/mm² and a particle size of 100–2,000 μm, and the primary particles thereof have an average particle size of at most 100 μm. The composition gives users neither an irritated feeling nor a feeling of physical disorder toward the skin and eyes, and a pleasant feeling upon use and has an excellent effect for improving a complexion.

17 Claims, No Drawings

COSMETIC COMPOSITION

BACKGROUND OF THE INVENTION

1. Field of the Invention

The present invention relates to a cosmetic composition which gives users neither an irritated feeling nor a feeling of physical disorder toward the skin and eyes, and a pleasant feeling upon use and has an excellent effect for facilitating the circulation of the blood to improve a complexion.

2. Description of the Background Art

Investigations as to various cosmetic compositions for facilitating the circulation of the blood have heretofore been made with the view toward preventing and improving the irregularity, dullness and lusterlessness of a complexion, which are caused by the irregularity of blood circulation. For example, cosmetic compositions (Japanese Patent Application Laid-Open Nos. 138411/1987 and 321616/1992, etc.) in which a blood circulation-facilitating agent is incorporated, and techniques (Japanese Patent Application Laid-Open Nos. 229926/1993, 320038/1993 and 9280/1994) in which the content of water is decreased to the utmost, and a polyol is incorporated at a high concentration so as to generate heat upon application and raise the temperature of the skin applied, thereby facilitating the circulation of the blood, and the like have been known.

However, the cosmetic compositions simply comprising the blood circulation-facilitating agent have required a high concentration of the blood circulation-facilitating agent or a long time in order that the effect of the blood circulation-facilitating agent may be recognized, and may have given users an irritated feeling toward the skin in some cases. On the other hand, the cosmetic compositions of the type that the temperature of the skin is raised have involved a problem that they have an abnormal feel of stickiness or sliminess and tend to give users a feeling of glow.

Massaging cosmetic compositions (Japanese Patent Application Laid-Open Nos. 44649/1976, 183205/1986, 211206/1988, 90011/1991 and 157279/1994) used for facilitating the circulation of the blood by applying physical irritation, massaging cosmetic compositions (Japanese Patent Application Laid-Open No. 44649/1976, Japanese Patent Publication No. 42203/1985, and Japanese Patent Application Laid-Open Nos. 192814/1983 and 295504/1988) to which particles are added for enhancing physical irritation have also been investigated. However, the massaging cosmetic compositions to which the particles are added have involved a problem that the effect of the particles are scarcely brought about when their particle size is smaller than 100 $\mu$m, and on the other hand, they give users a feeling of physical disorder during use, and damage the skin if the amount of time used or the frequency of use becomes high when the particle size is not smaller than 100 $\mu$m.

Further, techniques for enhancing safety by using granules which are gradually disintegrated by inunction or massaging have come to be investigated (Japanese Patent Publication No. 39444/1992, and Japanese Patent Application Laid-Open Nos. 221826/1993 and 271417/1994). Even when such granules have been used, however, the resulting cosmetic composition has given users an irritated feeling and a feeling of physical disorder toward the skin and eyes and have had no sufficient effect for facilitating the circulation of the blood.

SUMMARY OF THE INVENTION

Accordingly, it is an object of the present invention to provide a cosmetic composition which gives users neither an irritated feeling nor a feeling of physical disorder toward the skin and eyes and has an excellent effect for facilitating the circulation of the blood to improve a complexion.

In view of the foregoing circumstances, the present inventors have carried out an extensive investigation. As a result, it has been found that cosmetic compositions comprising granules having specific compression strength and particle size give users neither an irritated feeling nor a feeling of physical disorder toward the skin and eyes, and a pleasant feeling upon use and facilitate the circulation of the blood to markedly improve a complexion, thus leading to completion of the present invention.

According to the present invention, there is thus provided a cosmetic composition comprising disintegrating granules composed of water-insoluble primary particles and a binder, wherein the disintegrating granules in the cosmetic composition have a compression strength of 0.002–0.1 kgf/mm$^2$ and a particle size of 100–2,000 $\mu$m, and the primary particles thereof have an average particle size of at most 100 $\mu$m.

Since the cosmetic composition according to the present invention contains the disintegrating granules having the specific strength, it gives users neither an irritated feeling nor a feeling of physical disorder toward the skin and eyes, and a pleasant feeling upon use and has an excellent effect for facilitating the circulation of the blood to improve a complexion.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

The disintegrating granules useful in the practice of the present invention are composed of water-insoluble primary particles and a binder.

Examples of the water-insoluble primary particles include powders of organic high-molecular compounds such as polyethylene, polystyrene, polyester, polyvinyl chloride, polyamide, polypropylene, nylon, polyvinylidene fluoride, polyurethane, acrylic resins, polysiloxane, crystalline cellulose, starch and derivatives thereof; and inorganic powders such as silica, alumina, talc, kaolin, titanium oxide, zinc oxide, quartz and calcium phosphate powders. These primary particles may be in any form of a spherical form, an indeterminate form and the like. However, the spherical form is particularly preferred from the viewpoint of safety.

Examples of the binder include water-insoluble binders such as animal and plant oils which are solid at ordinary temperature, such as hydrogenated fish oil, hydrogenated castor oil and hydrogenated rapeseed oil; and water-soluble binders such as organic high-molecular compounds such as ethyl cellulose, acetyl cellulose, nitrocellulose, hydroxymethyl cellulose, hydroxyethyl cellulose, hydroxypropyl cellulose, polyvinyl pyrrolidone, polyvinyl acetate and polyvinyl alcohol. Of these, the combined use of the water-soluble binder and the water-insoluble binder is particularly preferred.

The disintegrating granules composed of these water-insoluble primary particles and binder can be prepared by a general granulating process, for example, fluidized bed granulation, agitation granulation or extrusion granulation. In particular, they may preferably be prepared in accordance with a process in which a water-insoluble binder is dissolved in an organic solvent, and the organic solvent is volatilized, thereby preparing granules (Japanese Patent Application Laid-Open No. 152407/1985), or a process in which powder of a water-insoluble binder is mixed with primary particles of granules, the mixture is granulated with a water-soluble binder, and the resultant granules are heated to melt the powder of the water-insoluble binder, and then cooled, thereby enhancing the water resistance of the granules (Japanese Patent Application Laid-Open No. 271417/1994).

Of such disintegrating granules, disintegrating granules obtained by using polyethylene particles as the primary particles, and hydroxypropyl cellulose and hardened rapeseed oil as the binder are preferred.

After incorporated into a cosmetic composition, the thus-obtained disintegrating granules in the cosmetic composition must have a compression strength of 0.002–0.1 kgf/mm$^2$, preferably 0.002–0.05 kgf/mm$^2$, more preferably 0.002–0.02 kgf/mm$^2$. If the compression strength is lower than 0.002 kgf/mm$^2$, the resulting cosmetic composition neither gives users a pleasant feeling upon use nor has a sufficient effect for improving a complexion. If the compression strength is higher than 0.1 kgf/mm$^2$ on the other hand, the resulting cosmetic composition strongly gives users an irritated feeling and a feeling of physical disorder.

The compression strength in the present invention is a value determined by taking an disintegrating granule out of the cosmetic composition or a bulk of the feed stock with tweezers carefully so as not to damage it, placing it on a specimen carrier of a Micro Compression Testing Machine (manufactured by Shimadzu Corporation) and measuring its compression strength by a method known per se in the art.

The particle size of the disintegrating granules in the cosmetic composition is within a range of 100–2,000 μm, preferably 100–1,000 μm, more preferably 200–600 μm. When the particle size falls within this range, the resulting cosmetic composition has a sufficient effect for improving a complexion and gives users no too strongly irritated feeling. It is hence preferable to use the disintegrating granules having a particle size within such a range. The average particle size of the primary particles of the granules in the cosmetic composition is at most 100 μm, preferably 1–20 μm, more preferably 3–15 μm. If the average particle size exceeds 100 μm, the resulting cosmetic composition gives users a too strongly irritated feeling after disintegration of the granules. It is hence not preferable to contain any primary particles having such a great average particle size.

These disintegrating granules may be used either singly or in any combination thereof and are preferably incorporated in a range of 0.1–5 wt. % (hereinafter indicated merely by "%"), more preferably 0.5–3%, most preferably 0.8–2% based on the total weight of the composition, because a cosmetic composition having a sufficient effect for improving a complexion and giving no feeling of physical disorder upon use can be provided.

The cosmetic compositions according to the present invention can be prepared by incorporating such disintegrating granules as the compression strength and particle size of the granules as well as the average particle size of the primary particles in the cosmetic compositions fall within the above respective ranges. Accordingly, no particular limitation is imposed on the disintegrating granules so far as they come to have the above-described features of the compression strength and the like after incorporated in the cosmetic compositions. No limitation is also imposed on the strength before incorporation. In view of disintegration of the granules during the preparation of a cosmetic composition, however, it is particularly preferable to use disintegrating granules having a compression strength of 0.01–0.5 kgf/mm$^2$ and a particle size of 100–2,000 μm before incorporation into the cosmetic composition, and the average particle size of primary particles of which is at most 100 μm.

In the cosmetic compositions according to the present invention, ingredients commonly used in the classical external skin care compositions, skin cleansing compositions, cosmetic compositions and massaging compositions, for example, oily substances, anti-melanogenic agents, sebum secretion inhibitors, blood circulation-facilitating agents, moisturizers, softeners, surfactants, keratin protecting agents, thickeners, antiseptics, pH adjusters, perfume bases, antioxidants, colorants, medicinally-effective agents, solvents, and the like, may be suitably incorporated in addition to the above-described components so far as no detrimental influence is thereby imposed on the effects of the present invention.

Examples of the oily substances include isotridecyl isononanoate, glyceryl tri-2-ethylhexanoate, neopentyl glycol dicaprate, 1-isostearoyl-3-myristoylglycerol, diisostearyl adipate, liquid isoparaffin, squalane, diglyceryl monoisostearate, diglyceryl diisostearate, diglyceryl triisostearate, glyceryl tri(caprylate caprate), isotridecyl myristate, octyldodecyl myristate, hexyldecyl myristate, octyldodecyl neodecanoate, evening primrose oil, jojoba oil, abocado oil, grape oil, turtle oil, mink oil, orange raffinate oil, polyoxyethylene- methyl polysiloxane copolymers, diglyceryl tetraisostearate, trimethylolpropane triisostearate, neopentyl glycol dioctanoate, diisostearyl malate, octyldodecyl lactate, 1,3-myristoylglycerol and isostearyl adipate.

Of these, isotridecyl isononanoate, neopentyl glycol dicaprate, 1-isostearoyl-3-myristoylglycerol, glyceryl tri-2-ethylhexanoate, squalane, 1,3-myristoyl-glycerol, diglyceryl monoisostearate, diglyceryl diisostearate, diglyceryl triisostearate and octyldodecyl lactate are preferred, with isotridecyl isononanoate, neopentyl glycol dicaprate and 1-isostearoyl-3-myristoylglycerol being particularly preferred.

These oily substances may be used either singly or in any combination thereof and are preferably incorporated in a proportion of 1–50%, particularly 3–17% based on the total weight of the composition.

The anti-melanogenic agents can serve to improve spots, freckles and a dark complexion caused by a melanin pigment, and as such agents, may be used, for example, ascorbic acid and derivatives thereof, hydroquinone derivatives, kojic acid and derivatives thereof, placenta extracts, plant extracts, and the like, which are printed in "Fragrance Journal, Extra Edition Vol. 14 (1995)" and are in common use as anti-melanogenic agents.

Specifically, examples of ascorbic acid and derivatives thereof include alkali metal salts of L-ascorbic acid phosphate such as sodium L-ascorbic acid phosphate and potassium L-ascorbic acid phosphate; alkaline earth metal salts of L-ascorbic acid phosphate such as magnesium L-ascorbic acid phosphate and calcium L-ascorbic acid phosphate; trivalent metal salts of L-ascorbic acid phosphate such as aluminum L-ascorbic acid phosphate; alkali metal salts of L-ascorbic acid sulfate such as sodium L-ascorbic acid sulfate and potassium L-ascorbic acid sulfate; alkaline earth metal salts of L-ascorbic acid sulfate such as magnesium L-ascorbic acid sulfate and calcium L-ascorbic acid sulfate; trivalent metal salts of L-ascorbic acid sulfate such as aluminum L-ascorbic acid sulfate; alkali metal salts of L-ascorbic acid such as sodium L-ascorbate and potassium L-ascorbic; alkaline earth metal salts of L-ascorbic acid such as magnesium L-ascorbate and calcium L-ascorbate; and trivalent metal salts of L-ascorbic acid such as aluminum L-ascorbate.

Examples of the hydroquinone derivatives include condensates of hydroquinone with a saccharide, such as arbutin, and condensates of an alkylhydroquinone obtained by introducing an alkyl group having 1–4 carbon atoms into hydroquinone with a saccharide.

Examples of kojic acid and derivatives thereof include kojic acid, monoesters such as kojic acid monobutyrate, kojic acid monocaprate, kojic acid monopalmitate, kojic acid monostearate, kojic acid monocinnamate and kojic acid monobenzoate, and diesters such as kojic acid dibutyrate, kojic acid dipalmitate, kojic acid distearate and kojic acid dioleate.

As the placenta extracts, may be used those generally sold as water-soluble placenta extracts and used as cosmetic raw materials. Examples thereof include those obtained by subjecting a placenta of a mammal such as bovine, swine or human to washing, depletion of blood, shredding, freezing and the like to extract a water-soluble component and then removing impurities from the water-soluble component.

Examples of the plant extracts include extracts from licorice, the root of kudzu, soybean, trillum, *Tulipa edulis, Anemarrhena asphodeloides* Bunge, *Ophiopogon japonicus* Ker-Gawler, sansevieria, white oak, *Artemisia capillaris* Thunb, chamomile, artichoke, aster, rice, clove, turmeric, balsam pear, aloe, tea plant, creeping saxifrage, *Scutellariae radix*, loquat, orange peel, ginseng, althea, cinchona quinine, comfrey, rosemary, lote, gulfweed and the like.

Of these, L-ascorbic acid, arbutin, kojic acid, placenta extracts, chamomile extract, tea plant extract, the extract of the root of kudzu and licorice extract are particularly preferred.

These anti-melanogenic agents may be used either singly or in any combination thereof and are preferably incorporated in a proportion of 0.01–10%, particularly 0.1–5% (in terms of dry solids content in the case of a plant extract) based on the total weight of the composition.

The sebum secretion inhibitors serve to prevent pigmentation and skin roughness around pores of the skin, pimple and the like caused by hypersteatosis, and as such agents, may be used, for example, anti-androgenic agents, crude drug extracts, astringents and the like, which are printed in "Fragrance Journal, Vol. 10 (1994)" and are in common use as sebum secretion inhibitors.

Specifically, examples of the anti-androgenic agents include oxendolone, 17-α-methyl-β-nortestosterone, chlormadinone acetate, cyproterone acetate, spironolactone, hydroxyflutamide, estradiol and ethinyl estradiol.

Examples of the crude drug extracts include extracts from leaves of walnut, *Scutellariae radix*, sage, hop, rosemary, Saint-Jone's-wort, Japanese mint, chamomile, cashew, goldthread, Amur cork tree, *Scutellaria baiculensis* Georgi (Labiatae), houttuyniae herba, dried orange peel, carrot, peony, Mat Rush, propolis, alismatis rhizoma, tannin, hamamelis, peony and birch tar, and royal jelly and yeast extract.

Examples of the astringents include zinc sulfocarbolate, zinc oxide, aluminum hydroxychloride and (allantoinato) dihydroxyaluminum.

Besides, vitamin $B_6$, 13-cis-retinoic acid, vitamin E, glycyrrhetinic acid, salicylic acid, nicotinic acid, calcium pantothenate, dicalcium azelate, 10-hydroxy-undecanoic acid, 12-hydroxystearic acid and the like may also be used as sebum secretion inhibitors.

Of these, estradiol, zinc sulfocarbolate, zinc oxide, royal jelly, 10-hydroxyundecanoic acid and 12-hydroxystearic acid are particularly preferred.

These sebum secretion inhibitors may be used either singly or in any combination thereof and are preferably incorporated in a proportion of 0.01–10%, particularly 0.1–5% (in terms of dry solids content in the case of a crude drug extract) based on the total weight of the composition.

Any agent may be used as the blood circulation-facilitating agent used in the present invention so far as it is an ingredient commonly used in the classical cosmetic compositions, quasi-drugs and drugs. For example, a simple compound, plant extract or the like may be used without any particular limitation.

Specifically, examples of the compound include esterified products, nicotinate and orotate of vitamin E, which are described as vasodilators in Japanese Patent Application Laid-Open No. 87506/1987; esterified products, acetate and succinate of vitamin E, which are described as periphery circulation-facilitating agents in Japanese Patent Application Laid-Open No. 195316/1987; and besides nicotinic acid amide, methyl nicotinate and the like. Examples of the plant extract include plant extracts which are clearly described as having a blood circulation-facilitating effect in "Fragrance Journal, Extra Edition Vol. 6 (1986)" and "Fragrance Journal, Extra Edition Vol. 1 (1979)", for example, extracts from arnica, hawthorn, cinchona quinine, Scarlet sage, *Tilia europaea* L, Panax Ginseng C. A. Meyer, juniper, rosemary, Saint-John's-wort, ginkgo, melissa, *Ononis spinosa* L, marronnier, Japanese green gentian, garlic, chamomile, Japanese mint, nettle, red pepper, ginger, hop, horse chestnut, lavender, carrot, brown mustard, cinnamon, pine, Cnidium ooficinale Makino, elder, Japanese parsley, *Scoploia japonica* Maxim, peony, myrica, *Houttuynia cordata*, candock, astringent persimmon, pot marigold, field poppy, gentian, grapes, *Glehnia littoralis*, bitter orange, citron, calamus, Watson pomelo, hamamelis, melilot, fennel, Japanese pepper tree, peony, eucalyptus, mugwort, Isodon Japonicus Hara, rice, *Sophoa flarescence* Aiton, zingiber, clove, Japanese linden and rice germ.

Of these, tocopherol nicotinate, nicotinic acid amide are preferred for the compounds, while Japanese green gentian extract, Japanese linden extract, zingiber tincture, Saint-Jone's-wort extract, ginkgo extract, arnica extract, hamamelis extract, pot marigold extract, marronnier extract, Isodon Japonicus Hara extract, scarlet sage extract, *Glehnia littoralis* extract, rice germ oil and *Tilia europaea* L extract are preferred for the plant extracts.

Tocopherol nicotinate, *Tilia europaea* L extract and Japanese linden extract are particularly preferred.

These blood circulation-facilitating agents may be used either singly or in any combination thereof and are preferably incorporated in a proportion of 0.001–5%, more preferably 0.01–3%, most preferably 0.02–2% based on the total weight of the composition, because a cosmetic composition having a sufficient effect for improving a complexion and giving no feeling of glow can be provided. Incidentally, in the case of the plant extract, the incorporated amount in terms of dry solids content should preferably fall within the above range.

No particular limitation is imposed on the moisturizers. However, examples thereof include ethylene glycol, diethylene glycol, triethylene glycol and still higher polyethylene glycols; propylene glycol, dipropylene glycol and still higher polypropylene glycols; butylene glycols such as 1,3-butylene glycol and 1,4-butylene glycol; glycerol, diglycerol and still higher polyglycerols; sugaralcohols such as sorbitol, mannitol, xylitol and maltitol; adducts of glycerols with ethylene oxide (hereinafter abbreviated as "EO") or propylene oxide (hereinafter abbreviated as "PO"); adducts of sugaralcohols with EO or PO; monosaccharides such as galactose and fructose, and EO or PO adducts thereof; polysaccharides such as maltose and lactose, and EO or PO adducts thereof; sodium pyrrolidonecarboxylate; and polyoxyethylene methylglucosides (number of moles of EO added: 10, 20, etc.).

Examples of the softeners include α-hydroxy acids such as α-hydroxyisobutyric acid, α-hydroxyisocaproic acid, α-hydroxy-n-capronic acid, α-hydroxyisocaprylic acid, α-hydroxy-n-caprylic acid, α-hydroxy-n-capric acid, lactic acid, α-hydroxystearic acid, citric acid and glycolic acid; basic amino acids such as lysine, arginine, histidine, ornithine and canavanine; amines such as ε-aminocaproic acid, urea, 2-hydroxyguanidine and 2-(2-hydroxyethoxy) ethylguanidine; and beside peptides described in Japanese Patent Application Laid-Open Nos. 99315/1987 and 178207/1990, and trimethylglycine described in Japanese Patent Application Laid-Open No. 293625/1994.

As the surfactant, any surfactant of nonionic surfactants, anionic surfactants, cationic surfactants and amphoteric surfactants may be used without any particular limitation. However, examples thereof include polyoxyethylene (hereinafter abbreviated as "POE") hardened castor oil, POE alkyl ethers, POE branched alkyl ethers, POE fatty acid esters, POE glycerol fatty acid esters, POE sorbitan fatty acid esters, POE sorbitol fatty acid esters, POE hardened castor oil alkylsulfates, POE alkyl sulfates, polyglycerol fatty acid esters, alkyl phosphates, POE alkyl phosphates, alkali metal salts of fatty acids, sorbitan fatty acid esters, glycerol fatty acid esters, alkyl polyglucosides, polyethylene glycol fatty acid esters, α-monoisostearyl glyceryl ether, sodium stearoyl methyltaurine, sodium POE lauryl ether phosphate and ether-modified silicones.

No particular limitation is imposed on the keratin protecting agents. However, examples thereof include mucopolysaccharides such as hyaluronic acid and chondroitin sulfate, proteins such as gelatin and collagen, and acid hetero-polysaccharides described in Japanese Patent Application Laid-Open No. 10997/1989.

No particular limitation is imposed on the thickeners. However, examples thereof include high-molecular compounds such as carrageenan, dextrin, methyl cellulose, ethyl cellulose, hydroxyethyl cellulose, hydroxypropyl cellulose, polyvinyl alcohol, polyacrylic acid, sodium polyacrylate, polymethacrylic acid, carboxyvinyl polymers, xanthan gum, carboxymethylchitin, chitosan and cationized cellulose, and inorganic compounds such as aluminum magnesium silicate and bentonite.

The cosmetic compositions according to the present invention may be provided as oil-based cosmetic compositions, water-based cosmetic compositions, emulsified cosmetic compositions, liquid crystal type cosmetic compositions or the like in any form of liquid, solid, paste, jelly, O/W emulsion, W/O emulsion and the like. In particular, they may preferably be provided as O/W type emulsified composition or water-based compositions. They may also be provided as compositions of such a type that they are only applied, that they are washed out after massaging, or that they are wiped out after massaging.

In the present invention, it goes without saying that taking the content of a solvent used as a base, for example, water or alcohol, into consideration upon incorporation of the disintegrating granules, disintegrating granules, which are not disintegrated by such a solvent, are chosen for use.

The cosmetic compositions according to the present invention may be used by applying them to a face, neck and/or the like by the conventional method. However, a higher effect may be brought about by manual massaging after application or inunction of the composition.

When the cosmetic composition is used with massaging or inunction, it is only necessary to take a necessary amount, for example, 2–4 g, of the composition in user's hand, lightly apply it to a face, neck and/or the like, lightly massage the part applied with the palm of the hand or the inner surfaces of fingers until the feel of the disintegrating granules disappears (about 30 seconds), and wipe the composition out with a tissue or cotton or wash it out with water or hot water.

The present invention will hereinafter be described in more detail by the following Examples. However, the present invention is not limited to these examples.

Incidentally, disintegrating granules used in the examples were as follows:

Disintegrating Granules A

Prepared by using 91 wt. % of primary particles (nylon powder; average particle size: 5 μm) and a binder (3 wt. % of hydrogenaed rapeseed oil+6 wt. % of hydroxypropyl cellulose) in accordance with the process described in Japanese Patent Application Laid-Open No. 271417/1994.

Compression strength: 0.06 kgf/mm$^2$

Average particle size: 350 μm.

Disintegrating Granules B

Prepared by using 94 wt. % of primary particles (nylon powder; average particle size: 5 μm) and 6 wt. % of a binder (ethyl cellulose) in accordance with the process described in Japanese Patent Application Laid-Open No. 271417/1994.

Compression strength: 0.015 kgf/mm$^2$

Average particle size: 450 μm.

Disintegrating Granules C

Prepared by using 93 wt. % of primary particles (nylon powder; average particle size: 5 μm) and a binder (6 wt. % of hydrogenated rapeseed oil+1 wt. % of hydroxypropyl cellulose) in accordance with the process described in Japanese Patent Application Laid-Open No. 271417/1994.

Compression strength: 0.019 kgf/mm$^2$

Average particle size: 511 μm.

Disintegrating Granules D

Prepared by using 89 wt. % of primary particles (nylon powder; average particle size: 5 μm) and a binder (5 wt. % of hydrogenatned rapeseed oil+6 wt. % of hydroxypropyl cellulose) in accordance with the process described in Japanese Patent Application Laid-Open No. 271417/1994.

Compression strength: 0.2 kgf/mm$^2$

Average particle size: 350 μm.

Disintegrating Granules E

Prepared by using 91 wt. % of primary particles (polyethylene powder; average particle size: 5 μm) and a binder (3 wt. % of hydrogenatned rapeseed oil+6 wt. % of hydroxypropyl cellulose) in accordance with the process described in Japanese Patent Application Laid-Open No. 271417/1994.

Compression strength: 0.15 kgf/mm$^2$

Average particle size: 400 μm.

EXAMPLE 1

(Oil-Based Cosmetic Composition)

Oil-based cosmetic compositions of their corresponding formulations shown in Table 1 were prepared in a method known per se in the art to evaluate them as to the absence of an irritated feeling, a feeling upon use and a blood circulation-facilitating effect. The results are shown in Table 1.

<Evaluation methods>

(1) Absence of an irritated feeling:

About 2 g of a sample cosmetic composition were applied to the cheek of each of six expert panelists and manually rubbed in the cheek, thereby organoleptically evaluating the composition as to an irritated feeling and a feeling of physical disorder toward the skin and eyes.

The composition was ranked as ○ where at least four panelists of the six panelists judged that the composition gave neither the irritated feeling nor the feeling of physical disorder, Δ where three panelists judged so, or X where at most two panelists judged so.

(2) Feeling upon use:

A sample cosmetic composition was organoleptically evaluated as to a pleasant feeling given by disintegration of the disintegrating granules in the same manner as in the evaluation as to the irritated feeling The composition was ranked as ○ where at least four panelists of the six panelists judged that the composition gave a pleasant feeling, Δ where three panelists judged so, or X where at most two panelists judged so.

(3) Blood circulation-facilitating effect:

About 1 g of a sample cosmetic composition was manually rubbed in the cheek of each of healthy persons (5 men and 6 women) aged 20 to 40 years. After the subject was given a 10-minute rest, a blood stream at the part applied was measured by means of a blood flowmeter (laser Doppler blood flowmeter manufactured by Biomedical Science Co.). The blood stream was also measured in the same manner as described above after a rest before the application of the cosmetic composition. Assuming that the respective blood streams are A and B, a percent increase of blood stream was determined in accordance with the following equation:

Percent increase of blood stream (VS) after a 10-minute rest:

$$VS=(A/B) \times 100 \ (\%)$$

On the other hand, the cheek of each of the subjects was massaged without applying the cosmetic composition to measure a blood stream at the part massaged. Assuming that a percent increase of blood stream at that time is VB, a blood circulation-facilitating effect (V) was determined in accordance with the following formula:

$$V=VS-VB$$

The blood circulation-facilitating effect was evaluated by giving a score 1 where V was greater than 0, or a score 0 where V was not greater than 0 to average the scores of the eleven subjects, and ranked as ○ where the average value was a score 1, or X where the average value was a score 0, when it was rounded at the first decimal place.

TABLE 1

| Component (%) | Invention product 1 | Comparative product 1 |
| --- | --- | --- |
| Disintegrating granules A | 5 | |
| Disintegrating granules C | | 5 |
| Sorbitan monooleate | 3 | 3 |
| Squalane | 92 | 92 |
| Compression strength (kgf/mm$^2$) | 0.005 | 0.001 |
| Particle size ($\mu$m) of disintegrating granules in cosmetic composition | 320 | 430 |
| Average particle size ($\mu$m) of primary particles | 5 | 5 |
| Absence of irritated feeling | ○ | ○ |
| Feeling upon use | ○ | X |
| Blood circulation-facilitating effect | ○ | X |

As apparent from the results shown in Table 1, the invention product gave users neither an irritated feeling nor a feeling of physical disorder toward the skin and eyes, and a pleasant feeling upon use. In addition, the invention product had an excellent effect for facilitating the circulation of the blood to improve a complexion.

EXAMPLE 2

(Water-Based Cosmetic Composition)

Water-based cosmetic compositions of their corresponding formulations shown in Table 2 were prepared in a method known per se in the art to evaluate them as to the absence of an irritated feeling, a feeling upon use and a blood circulation-facilitating effect in the same manner as in Example 1. The results are shown in Table 2.

TABLE 2

| Component (%) | Invention product 2 | Comparative product 2 | Comparative product 3 |
| --- | --- | --- | --- |
| Disintegrating granules A | 5 | | |
| Disintegrating granules B | | 5 | |
| Disintegrating granules D | | | 5 |
| Polyethylene (20) sorbitan monostearate | 3 | 3 | 3 |
| Glycerol | 10 | 10 | 10 |
| Purified water | 82 | 82 | 82 |
| Compression strength (kgf/mm$^2$) | 0.006 | 0.001 | 0.2 |
| Particle size ($\mu$m) of disintegrating granules in cosmetic composition | 330 | 400 | 300 |
| Average particle size ($\mu$m) of primary particles | 5 | 5 | 5 |
| Absence of irritated feeling | ○ | ○ | X |
| Feeling upon use | ○ | X | X |
| Blood circulation-facilitating effect | ○ | X | ○ |

As apparent from the results shown in Table 2, the invention product gave users neither an irritated feeling nor a feeling of physical disorder toward the skin and eyes, and a pleasant feeling upon use. In addition, the invention product had an excellent effect for facilitating the circulation of the blood to improve a complexion.

EXAMPLE 3

(Oil-in-Water Type Emulsified Cosmetic Composition)

Oil-in-water type emulsified cosmetic compositions of their corresponding formulations shown in Table 3 were prepared in a method known per se in the art to evaluate them as to the absence of an irritated feeling, a feeling upon use and a blood circulation-facilitating effect in the same manner as in Example 1. The results are shown in Table 3.

TABLE 3

| Component (%) | Invention product 3 | Comparative product 4 |
| --- | --- | --- |
| Disintegrating granules A | 5 | |
| Disintegrating granules B | | 5 |
| Sorbitan monooleate | 1 | 1 |
| Polyoxyethylene (20) sorbitan monooleate | 5 | 5 |
| Squalane | 10 | 10 |
| Glycerol | 10 | 10 |
| Purified water | 69 | 69 |
| Compression strength (kgf/mm$^2$) | 0.006 | 0.001 |
| Particle size ($\mu$m) of disintegrating granules in cosmetic composition | 300 | 390 |
| Average particle size ($\mu$m) of primary particles | 5 | 5 |
| Absence of irritated feeling | ◯ | ◯ |
| Feeling upon use | ◯ | X |
| Blood circulation-facilitating effect | ◯ | X |

As apparent from the results shown in Table 3, the invention product gave users neither an irritated feeling nor a feeling of physical disorder toward the skin and eyes, and a pleasant feeling upon use. In addition, the invention product had an excellent effect for facilitating the circulation of the blood to improve a complexion.

EXAMPLE 4
(Water-in-Oil Type Emulsified Cosmetic Composition)

Water-in-oil type emulsified cosmetic compositions of their corresponding formulations shown in Table 4 were prepared in a method known per se in the art to evaluate them as to the absence of an irritated feeling, a feeling upon use and a blood circulation-facilitating effect in the same manner as in Example 1. The results are shown in Table 4.

TABLE 4

| Component (%) | Invention product 4 | Comparative product 5 |
| --- | --- | --- |
| Disintegrating granules A | 5 | |
| Disintegrating granules C | | 5 |
| Sorbitan monooleate | 1 | 1 |
| Sorbitan monostearate | 5 | 5 |
| Squalane | 10 | 10 |
| Neopentyl glycol dicaprate | 20 | 20 |
| Glycerol | 30 | 30 |
| Purified water | 29 | 29 |
| Compression strength (kgf/mm$^2$) | 0.008 | 0.001 |
| Particle size ($\mu$m) of disintegrating granules in cosmetic composition | 290 | 480 |
| Average particle size ($\mu$m) of primary particles | 5 | 5 |
| Absence of irritated feeling | ◯ | ◯ |
| Feeling upon use | ◯ | X |
| Blood circulation-facilitating effect | ◯ | X |

As apparent from the results shown in Table 4, the invention product gave users neither an irritated feeling nor a feeling of physical disorder toward the skin and eyes, and a pleasant feeling upon use. In addition, the invention product had an excellent effect for facilitating the circulation of the blood to improve a complexion.

EXAMPLE 5

A cosmetic composition of a formulation shown below was prepared in a method known per se in the art.

| (Component) | (wt. %) |
| --- | --- |
| Disintegrating granules E | 2 |
| dl-α-Tocopherol nicotinate | 1 |
| Polyoxyethylene (60 EO) hardened castor oil | 2 |
| Carboxyvinyl polymer | 0.5 |
| Squalane | 10 |
| Glycerol | 10 |
| Polyoxyethylene (20 EO) sorbitan monostearate | 1 |
| Purified water | Balance |

The disintegrating granules in the resultant cosmetic composition had a compression strength of 0.004 kgf/mm$^2$ and a particle size of 350 $\mu$m, and the primary particles thereof had an average particle size of 5 $\mu$m.

The cosmetic composition was evaluated as to the absence of an irritated feeling, a feeling upon use and a blood circulation-facilitating effect in the same manner as in Example 1. As a result, it was judged to be excellent in all the items.

EXAMPLE 6

A cosmetic composition of a formulation shown below was prepared in a method known per se in the art.

| (Component) | (wt. %) |
| --- | --- |
| Disintegrating granules E | 2 |
| dl-α-Tocopherol nicotinate | 1 |
| Tilia europaea L extract | 1 |
| Polyoxyethylene (40 EO) hardened castor oil | 2 |
| Polyoxyethylene (20 EO) sorbitan monostearate | 1 |
| Carboxyvinyl polymer | 0.2 |
| Sodium carboxymethyl cellulose | 0.2 |
| Triglycopolysaccharide | 0.2 |
| Glycerol | 10 |
| Squalane | 10 |
| L-Arginine | 0.5 |
| Methyl polysiloxane | 2 |
| Cetanol | 1 |
| p-Hydroxybenzoic acid ester | 0.1 |
| Purified water | Balance |

The disintegrating granules in the resultant cosmetic composition had a compression strength of 0.006 kgf/mm$^2$ and a particle size of 360 $\mu$m, and the primary particles thereof had an average particle size of 5 $\mu$m.

The cosmetic composition was evaluated as to the absence of an irritated feeling, a feeling upon use and a blood circulation-facilitating effect in the same manner as in Example 1. As a result, it was judged to be excellent in all the items.

EXAMPLE 7

A cosmetic composition of a formulation shown below was prepared in a method known per se in the art.

| (Component) | (wt. %) |
| --- | --- |
| Disintegrating granules E | 2 |
| dl-α-Tocopherol nicotinate | 1 |
| Japanese linden extract | 1 |
| Polyoxyethylene (60 EO) hardened castor oil | 2 |
| Polyoxyethylene (20 EO) sorbitan monostearate | 1 |
| Carboxyvinyl polymer | 0.2 |
| Sodium carboxymethyl cellulose | 0.3 |
| Stearyl alcohol | 0.5 |

-continued

| (Component) | (wt. %) |
| --- | --- |
| Isotridecyl isononanoate | 5 |
| Glycerol | 5 |
| 1,3-Butylene glycol | 5 |
| Polyethylene glycol | 1 |
| Methyl polysiloxane | 2 |
| Perfume base | 0.02 |
| Purified water | Balance |

The disintegrating granules in the resultant cosmetic composition had a compression strength of 0.003 kgf/mm$^2$ and a particle size of 350 μm, and the primary particles thereof had an average particle size of 5 μm.

The cosmetic composition was evaluated as to the absence of an irritated feeling, a feeling upon use and a blood circulation-facilitating effect in the same manner as in Example 1. As a result, it was judged to be excellent in all the items.

EXAMPLE 8
(Cleansing Gel)

A cleansing gel of a formulation shown below was prepared in a method known per se in the art.

| (Component) | (wt. %) |
| --- | --- |
| Polyoxyethylene (20 EO) octyldodecanol | 9.7 |
| Polyoxyethylene (20 EO) sorbitan monostearate | 7.5 |
| Polyoxyethylene (20 EO) sorbitan monoisostearate | 7.5 |
| Sorbitan monostearate | 0.25 |
| Sorbitan monooleate | 0.7 |
| Carrageenan | 0.6 |
| BHT | 0.1 |
| Cocamodo MEA | 0.2 |
| Sorbitol (70% in water) | 60.0 |
| Magnesium laurate sulfate | 0.5 |
| KCl | 0.1 |
| MgSO$_4$ | 0.2 |
| Purified water | 7.55 |
| Disintegrating granules F | 5.0 |

*Disintegrating granules F: Prepared by using 96.2 wt. % of primary particles (polyethylene powder; average particle size: 45 μm) and 3.8 wt. % of a binder (hydroxypropyl cellulose) in accordance with the process described in Japanese Patent Application Laid-Open No. 271417/1994.
Compression strength: 0.068 kgf/mm$^2$
Average particle size: 605 μm.

The disintegrating granules in the resultant cosmetic composition had a compression strength of 0.053 kgf/mm$^2$ and a particle size of 550 μm, and the primary particles thereof had an average particle size of 45 μm.

The cosmetic composition was evaluated as to the absence of an irritated feeling, a feeling upon use and a blood circulation-facilitating effect in the same manner as in Example 1. As a result, it was judged to be excellent in all the items.

What is claimed is:

1. A cosmetic composition, comprising disintegrating granules composed of water-insoluble primary particles and a binder, wherein the disintegrating granules in the cosmetic composition have a compression strength of about 0.002–0.1 kgf/mm$^2$ and a particle size of about 100–2,000 μm, wherein the primary particles thereof have an average particle size of at most about 100 μm, and wherein the water-insoluble primary particles are particles selected from the group consisting of polyethylene, polystyrene, polyester, polyvinylchloride, polyamide, polypropylene, nylon, polvinylidene fluoride, polyurethane, acrylic resins, polysiloxane, crystalline cellulose, starch, silica, alumina, talc, kaolin, titanium oxide, zinc oxide, quartz and calcium phosphate.

2. The cosmetic composition according to claim 1, wherein the disintegrating granules before incorporated in the cosmetic composition have a compression strength of 0.01–0.5 kgf/mm$^2$ and a particle size of 100–2,000 μm, and the primary particles thereof have an average particle size of at most 100 μm.

3. The cosmetic composition according to claim 1, wherein the binder is composed of a water-soluble binder and a water-insoluble binder.

4. The cosmetic composition according to claim 3, wherein the water-soluble binder is selected from the group consisting of ethyl cellulose, acetyl cellulose, nitrocellulose, hydroxymethyl cellulose, hydroxyethyl cellulose, hydroxypropyl cellulose, polyvinyl pyrrolidone, polyvinyl acetate and polyvinyl alcohol, and the water-insoluble binder is an animal or plant oil which is solid at ordinary temperature.

5. The cosmetic composition according to claim 1, wherein the water-insoluble primary particles are composed of polyethylene, and the binder is composed of hydroxypropyl cellulose and hydrogenated rapeseed oil.

6. The cosmetic composition according to claim 3, wherein the disintegrating granules is incorporated in an amount of 0.1–5 wt. % based on the total weight of the composition.

7. The cosmetic composition according to claim 1, which is used by applying it to the skin and massaging the part applied.

8. The cosmetic composition according to claim 1, wherein said water-insoluble primary particles are spherical in shape.

9. The cosmetic composition according to claim 4, wherein both water-soluble binder and water-insoluble binder are used.

10. The cosmetic composition according to claim 1, wherein said disintegrating granules have a particle size of about 100–1,000 μm.

11. The cosmetic composition according to claim 10, wherein said disintegrating granules have a particle size of about 200–600 μm.

12. The cosmetic composition according to claim 1, wherein the water-insoluble primary particles have an average particle size of about 1–20 μm.

13. The cosmetic composition according to claim 12, wherein the water-insoluble primary particles have an average particle size of about 3–15 μm.

14. The cosmetic composition according to claim 1, wherein said cosmetic composition is an external skin care composition.

15. The cosmetic composition according to claim 1, wherein said cosmetic composition is a skin cleansing composition.

16. The cosmetic composition according to claim 1, wherein said cosmetic composition is a massaging composition.

17. The cosmetic composition according to claim 1, wherein said cosmetic composition is in a form comprising liquid, solid, paste, jelly, O/W emulsion or W/O emulsion.

* * * * *